US008580745B2

(12) United States Patent
Borodic

(10) Patent No.: US 8,580,745 B2
(45) **Date of Patent: *Nov. 12, 2013**

(54) COMPOSITION FOR THERAPEUTIC AND COSMETIC BOTULINUM TOXIN

(75) Inventor: Gary Borodic, Canton, MA (US)

(73) Assignee: Botulinum Toxin Research Associates Inc., Quincy, MA (US)

( * ) Notice: Subject to any disclaimer, the term of this patent is extended or adjusted under 35 U.S.C. 154(b) by 1572 days.

This patent is subject to a terminal disclaimer.

(21) Appl. No.: 11/709,059

(22) Filed: Feb. 22, 2007

(65) Prior Publication Data

US 2011/0172161 A1 Jul. 14, 2011

Related U.S. Application Data

(63) Continuation of application No. 10/446,562, filed on May 28, 2003, now Pat. No. 7,459,164.

(60) Provisional application No. 60/383,750, filed on May 28, 2002.

(51) Int. Cl.

| | |
|---|---|
| ***A61K 38/16*** | (2006.01) |
| ***A61K 39/08*** | (2006.01) |
| ***A61P 17/00*** | (2006.01) |

(52) U.S. Cl.
USPC ........ 514/21.2; 514/18.8; 424/239.1; 424/9.1

(58) Field of Classification Search
USPC .......... 424/239.1, 236.1, 9.1; 514/2, 12, 21.2, 514/18.8; 530/350; 435/252.7
See application file for complete search history.

(56) References Cited

U.S. PATENT DOCUMENTS

| | | | | |
|---|---|---|---|---|
| 4,861,627 | A | 8/1989 | Mathiowitz et al. | |
| 5,069,936 | A | 12/1991 | Yen | |
| 5,512,547 | A | 4/1996 | Johnson et al. | |
| 5,576,468 | A | 11/1996 | Lubowitz | |
| 5,696,077 | A | 12/1997 | Johnson et al. | |
| 5,756,468 | A | 5/1998 | Johnson et al. | |
| 5,846,929 | A | 12/1998 | Johnson et al. | |
| 6,100,306 | A | 8/2000 | Li et al. | |
| 6,210,707 | B1 | 4/2001 | Papahadjopoulos et al. | |
| 6,312,706 | B1 | 11/2001 | Lai et al. | |
| 6,620,617 | B2 | 9/2003 | Mathiowitz et al. | |
| 7,459,164 | B2 * | 12/2008 | Borodic | 424/239.1 |
| 7,491,403 | B2 * | 2/2009 | Borodic | 424/239.1 |
| 7,691,394 | B2 * | 4/2010 | Borodic | 424/239.1 |
| 2002/0064536 | A1 | 5/2002 | Hunt | |
| 2003/0138437 | A1 | 7/2003 | Hunt | |
| 2004/0126396 | A1 | 7/2004 | Aoki et al. | |
| 2004/0151741 | A1 | 8/2004 | Borodic | |

FOREIGN PATENT DOCUMENTS

| | | |
|---|---|---|
| WO | WO 94/00481 | 1/1994 |
| WO | WO 97/35604 | 10/1997 |
| WO | WO 01/58472 A2 | 8/2001 |

OTHER PUBLICATIONS

Borodic, "Botulinum A Toxin for (expressionistic) ptosis overcorrection after frontalis sling," Ophtalmic Plastic & Recostructive Surg. 8(2): 137-142, (1992).
Borodic et al. Botulinum A Toxin for the treatment of spasmodic torticollis, Dysphagia and Regional Toxin Spread. Head & Neck, 12: 392-398 (1990).
Nussgens et al. "Comparison of two botulinum-toxin preparations in the treatment of essential blepharospasm," Graefes Arch Clin Exp Ophthalmol 235(4): 197-199 (1997).
Bigalke et al. Botulinum A Toxin: Dysport improvement of biological availability,: Exp. Neurol. 168(1): 162-170 (2001).
Lew et al. "Botulinum toxin type B: a double-blind, placebo-controlled, safety and efficacy study in cervical dystonia," Neurology 49(3): 701-707 (1997).
Borodic et al "Botulinum Toxin: Clinical and Scientific Aspects." Ophthalmology Clinics of North America 4: 491-503 (1991).
Borodic et al "Botulinum: a toxin for spasmodic torticollis, multiple vs single injection points per muscle," Head and Neck 14:33-37 (1992).
Ranoux et al "Respective potencies of Botox and Dysport: a double blind, randomized, crossover study in cervical dystonia," J. Neuro. Neurosurg. Psychiatry 72: 459-462 (2002).
Borodic et al., "Botulinum toxin therapy, immunologic resistance, and problems with available materials," Views and Reviews, Neurology 1996; 46:26-29.
Borodic et al., "Botulinum B Toxin as an Alternative to Botulinum A Toxin, A Histologic Study," Opthalmic Plastic and Reconstructive Surgery 9(3): 182-190 (1993).
Journal of Clin Anesth. 11(7): 615-6, Troll et al. (1999).
Borodic et al. "Botulinum A Toxin for Treatment of Aberrant Facial Nerve Regeneration," Plastic and Reconstructive Surger, (91)6: 1042-1045, 1993.
Borodic, Gary "Botulinum toxin: issues and application," Current Opinion in Otolaryngology & Head and Neck Surgery, 1999, 7:219-255.
Acquadro, Martin A. et al. "Treatment of Myofascial Pain with Botulinum A Toxin," Anesthesiology, vol. 80, No. 3, Mar. 1994.
Schantz, Edward J. et al. "Standardized Assay for Clostridium botulinum Toxins," Journal of the AOAC, vol. 61, No. 1, 1978.

* cited by examiner

*Primary Examiner* — Chih-Min Kam
(74) *Attorney, Agent, or Firm* — Milbank, Tweed, Hadley & McCloy LLP

(57) ABSTRACT

This invention relates to a composition of botulinum based pharmaceuticals used for therapeutic and cosmetic treatment. This invention offers an improvement on the prior art by eliminating the potential of blood-borne contamination with botulinum based pharmaceuticals. Recombinant serum albumin is taught for use in the place of human serum albumin as a stabilizing or enhancing agent.

22 Claims, No Drawings

COMPOSITION FOR THERAPEUTIC AND COSMETIC BOTULINUM TOXIN

This application is a continuation of U.S. patent application Ser. No. 10/446,562, filed on May 28, 2003, which matured into U.S. Pat. No. 7,459,164, and claims priority to U.S. Provisional Patent Application Ser. No. 60/383,570, filed May 28, 2002. The disclosures of the referenced applications are hereby incorporated by reference in their entirety.

FIELD OF INVENTION

This invention relates to a composition of botulinum based pharmaceuticals used for therapeutic and cosmetic treatment. This invention offers an improvement on the prior art by eliminating the potential of blood-borne contamination with botulinum based pharmaceuticals.

BACKGROUND OF THE INVENTION

Human serum albumin ("HSA") is used to stabilize botulinum toxin at high dilutions. This albumin is a human blood product-derived agent from pooled plasma collections. As the molecular weight of the material is low (69,000), filtration generally allows for excellent filtration sterilization, however, prions (non-nucleic acid dependent infectious agents) have become an increasing concern for both federal regulators and the general public. Most physicians and patients do not even know that there are human blood products within BOTOX™, the market leading botulinum toxin product. Prion dependent diseases include Creutzfeld-Jacob disease, Kuru, fatal familial insomnia, and Gertmann-Straussler-Scheinker disease. Although the incidences of these diseases are rare (one in 1,000,000), it has been estimated that one in 10,000 are infected with prions at the time of death. Prion diseases generally cause spongiforma encephalopathies of the brain with serious attendant neurologic symptoms prior to death. Humans are thought to acquire prions in two ways: (1) infection from medical procedures such as surgery, biologic agents, and tissue transplants, and (2) genetically. The impact that these observations have made is to try to limit human blood products in biologic agents.

Recently, recombinant albumin (RECOMBUMIN™) has become available via Delta Biotechnology LTD, (Nottingham, UK-Aventis-Behring LLC) via high yield yeast expression system, offering a synthetic alternative to human serum albumin and an important differential point. In clinical studies including 500 patients, there have been comparable immunity and allergic reactions to native HSA, although larger study figures may be available at this time.

HSA has been employed as a stabilizer in botulinum toxin since its introduction into clinical studies in 1981 (see Schantz E., Johnson E. Therapy with Botulinum Toxin, Mercel Dekker, New York, 1994). The purpose of the albumin protein in high concentration relative to the botulinum neurotoxin is to maintain structural and biologic integrity of the toxin during and after the dilution steps in manufacturing pharmaceutically acceptable doses. The albumin appears to bind (via non-covalent molecular interaction) with the neurotoxin, preventing adherence of toxin molecules to the glass containers and protecting the tertiary structures on the protein molecule from disruption when diluted in aqueous solution.

Botulinum toxin has been stabilized by a number of proteins, hence there are multiple opportunities to remove the human serum albumin from the formulation. Such proteins include, but are not limited to, animal based gelatins, ovalbumin, lysozyme, bovine and porcine albumins. HSA has been the preferred stabilizer primarily because of its low immungenicity. Anaphylastic or analphylactoid reaction, although possible, are low with use of human albumin compared to other protein stabilizers such as gelatins, which have reactivity rates as high as 0.5-1%. The reactivity rate of albumin has been estimated at less than 0.1%, although generalized urticaria syndrome has rarely been observed with human albumin, in a frequency similar to a common blood transfusion reaction. As gelatins have been associated with much higher local and generalized allergic reactions, these categories of proteins are not suitable excipients. Because of the need for repeated injections required to treat many clinical indications and uses, any stabilizing excipient in a botulinum toxin product must have a low immunoreactivity rate.

Infectious risks of HSA include hepatitis and other infectious agents, which have been eliminated for decades by pasteurization of pooled blood serum. As donor lots typically may come from as many as 50,000 individuals, rigorous standards of processing are necessary. As pasteurization does not eliminate prions, however such measures fo not eliminate the risk of transmission of prions by human blood products, such as HAS. Prion based disease transmission has been demonstrated by transfusing infected donor blood among animal species. In humans, possible transmission has been reported after corneal transplantation and other tissue transplantation procedures. It has been suggested that the disease can be genetically transmitted. The major public risks to prion-based diseases relate specifically to the inability to sterilize animal and human based products from the infectious agent. Conventional gas and heat sterilization have not been reliable, nor have filtration techniques such as those used to prepare botulinum toxin based pharmaceuticals.

Diseases identified to be caused by prions include Creutzfeld-Jacob disease, Kuru, fatal familial insomnia, and Gertmann-Straussler-Scheinker disease. Creutzfeld Jacob disease and its veterinary correlate ("mad cow disease") is an encephalopathy which progressively impairs neurologic function causing seizures, dementia, somnolence, and death over a period of months to several years. Incubation periods may be as long as ten years so immediate analysis and elimination of sources of contamination may not be possible. Such a public health risk demands a strict approach to elimination of possible sources and opportunity for transmission. Recently, a blood donor to the albumin pool was reported retrospectively to have contracted Creutzfeld Jacob disease after having contributed to the albumin pool. Fortunately, no one appears to have contracted prion-based diseases to date from the use of human serum albumin within pharmaceuticals or when used as a plasma expander.

The incidence of prion based disease is rare (1:1,000,000) although it has been estimated that 1:10,000 autopsy analyzed human brains indicate infection at time of death. The pathology is described as a subacute spongiform change, which can be seen on microscopic examination of the neocortex. Even at a incidence of 1 per million, the chance that at least one blood donor contributing to the albumin pool over a twenty year period will be infected is high even with strict standards of screening. To date there are no validated tests to assess a blood donor for the syndrome. Many patients treated with botulinum based pharmaceuticals will need repeated injections over a twenty to thirty year period and so run a repeated risk of exposure.

In recent years, blood collecting centers have been mandated by regulatory agencies to screen for foreign travel exposure to areas where prion-related diseases have been reported, such as Great Britain, and such donors are excluded from the donor source for pharmaceutical grade albumin (see Reuters News Agency-1999 releases). Despite major worldwide effort to prevent international and intercontinental cross contamination, mad cow disease has recently been reported in Canada in May, 2003. The mode of transmission whether genetic or via contamination needs to be determined.

In recent years, there has been increasing consumption of botulinum toxin for cosmetic use as compared to its original medicinal indications, such as blepharospasm, spasmodic torticollis spasticity and other involuntary movement disorders. Because of the more casual use of this agent for cosmetic purposes, concerns arose over inadvertent exposure of large numbers of patients to human blood products via albumin. In past publications (Borodic GE Botulinum toxin issues and applications, Current Opinions in Otolaryngology, 1998 Dec. 5; 352(9143):1832), the disadvantages of human blood products within the vials of botulinum toxin were cited, especially relative to its use as a cosmetic agent. Physicians have not been routinely advising patients of the presence of human blood products although the major manufacturer of one form of botulinum toxin (BOTOX™) has listed the risk of possible prion contamination on its package insert.

SUMMARY OF THE INVENTION

This invention relates to a composition of botulinum based pharmaceuticals used for therapeutic and cosmetic treatment. This invention offers an improvement on the prior art by eliminating the potential of blood-borne contamination with botulinum based pharmaceuticals. Recombinant serum albumin is taught for use in the place of human serum albumin as a stabilizing or enhancing agent.

In one aspect, the invention features a pharmaceutical composition comprising a botulinum neurotoxin formulated with a recombinant serum albumin. In another aspect, the invention features a pharmaceutical composition comprising a botulinum cytotoxin formulated with a recombinant serum albumin.

DESCRIPTION OF THE INVENTION

Given the more casual use of botulinum toxins for cosmetic use, the possible presence of prion-based disease in low incidence in the population and the use of large pooled quantities of human serum albumin from thousands of blood donors, it would be useful to replace the HSA with a nonhuman or bovine sourced albumin.

Botulinum Toxin Manufacturing Specifications:

Botulinum toxin is prepared from various strains of *Clostridia botulinum* by fermentation and separation of the protein from spent cultures. Such separation techniques initially involve acid precipitation done in multiple steps causing removal of exogenous proteins and other particulate matter, according to the methods outlined by Schantz and Johnson. Final separation is further accomplished with chromatographic methods yielding a high specific toxicity. The biologic activity of botulinum toxin is generally measured by an LD 50 bioassay, using a 20-30 gram Swiss Webster mouse. Specific toxicity is measured using LD 50 units over nanograms of botulinum neurotoxin or cytotoxin protein. It is appreciated that certain immunotypes of non-A botulinum toxin have not been crystallized by the Schantz precipitation techniques and for such immunotypes the method of separation is limited to chromatographic techniques.

The strain of *Clostridia botulinum* may produce any immunotype. Generally a given strain produces usually one immunotype A-G. Certain strains produce exclusively cytotoxin (non-neurotoxin) and such strains can be a source of pharmaceutically active agents. The preferred strain for the production of immunotype A is the Hall strain, which has been previously qualified to produce a highly bioactive toxin (greater than 10 million mouse LD 50 units per milliliter).

Once full crystallization of botulinum toxin is accomplished, sterilization is conducted using filtration techniques. A dilution with protein-containing solution is done to achieve pharmaceutically active dose forms. To confirm each dose form is retained according to the dilution method, another LD 50 bioactivity assay is performed to maintain quality control. It is critical that the diluent contains a stabilizing protein. The preferred protein is recombinantly-produced human albumin from an recombinant yeast carrier, such as *Saccharomyces cerevisiae* or *Pichia pastoris*. The recombinant serum albumin is inserted into the diluent. For stabilization and shelf life preservation, freeze drying or flash drying may be utilized. Alternatively, pH adjustment can be used to enhance shelf life.

pH and Composition:

Generally, a pH of 7.4 is desirable in the final composition of the fluid prior to the freeze drying preservation process. This pH results in a more tolerable degree of discomfort to the patient upon injection of the final formulation. Lower pH formulations are associated with a much higher degree of pain upon injection. Lower pH formulations, however, enhance preservation of botulinum toxin and extend shelf life. Recombinant serum albumin may be used either in liquid or freeze dried formulation.

Immunogenicity and Allergic Properties of Recombinant Serum Albumin:

Early generations of manufactured recombinant serum albumin were limited in utility by the presence of immunogens which cause local inflammation after repeated injections. Botulinum-based pharmaceutical preparations require repeated injections, usually at three to four month intervals. If the recombinant serum albumin contains a critical mass of foreign extraneous yeast proteins, local and systemic inflammation may occur after repeated injections. In test samples, the separation of exogenous proteins was inadequate, hence local and systemic erythema and edema were noted in a significant numbers of test subjects receiving early generations of recombinant albumin. Such preparations were poor choices as a stabilizer, as the stabilizer appeared to cause more drug-induced allergic complications than the active agent. The recombinant serum albumin must be qualified with respect to local allergy at a rate of less than 1% for the preparation to meet a minimally acceptable standard. Any local or systemic allergic response to the recombinant serum albumin would make the use of the botulinum toxin unfeasible, with an adverse risk/benefit ratio for the patient.

Recombinant Serum Albumin Concentration and Botulinum Toxin Based Pharmaceutical Preparations:

The utility of adjuvant proteins has been appreciated since the inception of botulinum toxin pharmaceutical technology. The importance of concentration however has not been appreciated until recently. The concentration of human albumin does play an important role in the LD 50 unit dosage for botulinum type A toxins. DYSPORT™ botulinum toxin, for instance, contains one forth the quantity of human serum albumin than BOTOX™ and such a difference has been associated with a decreased potency relative to the LD 50 unit dosage (Biglalke et al (Exp Neurol 2001 March, 168(1):162-70 Botulinum A toxin: Dysport improvement of biological availability). Such differences relate to pharmacokinetic factors attributable to a direct chemical reaction of the albumin with the botulinum neurotoxin. Non-covalent binding via electrostatic or Van der Waals forces between molecules may contribute to botulinum sequestration necessary for effective binding with botulinum toxin on nerve tissues or possibly other binding sites.

Recently, higher albumin concentration-containing injection formulations have proven to be more effective than the usual 0.5 mg/vial concentration conventionally used in BOTOX for certain patients, as demonstrated by the following case:

NM is a 53 year old woman with a three year history of involuntary blepharospasm causing difficulty driving and maintaining employment. She had been treated with increasing doses of BOTOX™ containing 0.5 mg albumin/vial in addition to the active neurotoxin complex with associated proteins. She sustained no improvement at doses in excess of 100 units injected into multiple peri-ocular locations. Therapeutic trials with artane and Clonipin failed to produce any therapeutic benefit. An attempt at up to 6000 units of Botulinum toxin type B also failed to produce any benefit. Limited myectomy surgery was performed on both eyelids without substantial lasting benefit. Because of multiple therapeutic failures, a vial of BOTOX™ was reformulated with concentrated albumin excipient to a concentration 10× that usually employed. The final concentration was 5 mg/vial. Repeat injection at the same dose of neurotoxin which previously failed produced an excellent result lasting at least one month with no side effects or complications.

A series of six patients, with poor results to BOTOX™, have been responsive to high albumin concentration botulinum toxin type A. Based on these observations, higher concentration albumin botulinum preparations would be preferable compared to commercially available preparations.

The observation of the use of higher albumin concentrations with Botulinum type A from BOTOX is contrary to in vitro experimentation for denervation potency in animals using a rat diaphragm model (see Bigalke H, Wohlfarth K., Irmer A., Dengler R. Exp Neurol. 2001 March, 168(1):162-70 Botulinum A toxin: Dysport improvement of biological availability). Wohlfarth could not produce an enhancement of the denervation and pharmacologic potency of BOTOX or other type A toxins using his in vitro animal experiments (International Congress, Hanover Germany, June 2002). His observations implicate an albumin interaction but does not explain the mechanistic importance of the relationship between botulinum toxin and albumin, and how such a relationship can be used to formulate superior pharmaceutical preparations when injected into living tissues subject to blood perfusion.

Described herein is a method by which larger amounts of albumin (greater than 0.5 milligrams per 100 International Units) can be used to enhance the chemodenervative and potency properties of botulinum toxin by sequestering the neurotoxin and allowing maximum binding with cell surface receptors by preventing the toxin from diffusing away from the injection field. In summary, higher concentrations of recombinant albumin are preferable in the formulation described herein. Following are examples of such a method:

1. A 50 year old woman wishing to have effacement of glabellar frown lines and transverse forehead lines, yet wishes no exposure to human blood products is injected with a dose of 10-300 mouse LD 50 units of botulinum toxin into frontalis and glabellar muscles in multiple location. Injections are repeated at three to four month intervals to maintain the desired effects.

2. A 60 year old patient with adult onset spasmodic torticollis not wishing exposure to human blood products with possible attendant risks of prion or other infectious agents wishes to be treated with botulinum immunotype A with no human blood products and higher degrees of stabilizing albumin to prevent diffusion into peripharyngeal musculature with possible attendant dysphagia presents to his physician. The physician injects a botulinum type A toxin with no human blood products and a concentration of recombinant serum albumin exceeding 0.5 mg/cc. using 20-1000 mouse LD 50 units.

3. A 50 year woman with myofascial pain, wishing relief from pain within the posterior cervical region, requests no exposure to human blood products for religious and medical reasons. The physician treats this patient with botulinum type A toxin stabilized with high concentration recombinant serum albumin (greater than 0.5 mg/cc) at a dose of 10-400 mouse LD 50 units. Repeated injections are conducted at various intervals.

4. A 70 year old woman with blepharospasm wishes relief from involuntary blinding eyelid spasms yet requests no exposure to human blood products. This woman is injected with a botulinum toxin preparation stabilized with recombinant serum albumin at a concentration greater than 0.5 mg/cc using between 5-150 mouse LD 50 units.

What is claimed is:

1. A composition comprising a botulinum neurotoxin formulated with a recombinant serum albumin for administration to a patient in need thereof, wherein said composition induces an allergic response of less than 1% of administrations.

2. The composition of claim 1, wherein said composition induces an allergic response of less than 1% after three injections.

3. The composition of claim 1, wherein said induced allergic response is local.

4. The composition of claim 3, wherein said allergic response is erythema or edema or both.

5. The composition of claim 1, wherein said allergic response is inflammation.

6. The composition of claim 1, wherein said allergic response is systemic.

7. The composition of claim 1, wherein said injections occur at three to four month intervals.

8. The composition of claim 1, wherein the concentration of said recombinant serum albumin is greater than 0.5 mg per 100 International Units botulinum neurotoxin.

9. The composition of claim 1, wherein the concentration of said recombinant serum albumin is greater than 0.5 mg/cc using 20-1000 mouse $LD_{50}$ units.

10. The composition of claim 1, wherein the concentration of said recombinant serum albumin is greater than 0.5 mg/cc using 10-300 mouse $LD_{50}$ units.

11. The composition of claim 1, wherein the concentration of said recombinant serum albumin is greater than 0.5 mg/cc using 10-400 mouse $LD_{50}$ units.

12. The composition of claim 1, wherein the concentration of said recombinant serum albumin is greater than 0.5 mg/cc using 5-150 mouse $LD_{50}$ units.

13. The composition of claim 1, wherein said botulinum neurotoxin is selected from the group consisting of immunotypes A, B, C, D, E, F and G.

14. The composition of claim 1, wherein said recombinant serum albumin is isolated from yeast.

15. The composition of claim 14, wherein said yeast is *Saccharomyces cerevisiae* or *Picchia pastoris.*

16. The composition of claim 1, wherein said botulinum neurotoxin is a chimeric protein or a combination of various botulinum toxin immunotypes.

17. The composition of claim 1, wherein said serum albumin is recombinant human serum albumin.

18. A method of treating blepharospasm comprising administering a therapeutically effective amount of the composition of claim 1 to a patient in need thereof to thereby treat said blepharospasm.

19. A method of effacing glabellar frown lines comprising administering a therapeutically effective amount of the composition of claim 1 to a patient in need thereof to thereby efface said glabellar frown lines.

20. A method of effacing transverse forehead lines comprising administering a therapeutically effective amount of the composition of claim 1 to a patient in need thereof to thereby efface said transverse forehead lines.

21. A method of treating spasmodic torticollis comprising administering a therapeutically effective amount of the composition of claim 1 to a patient in need thereof to thereby treat spasmodic torticollis.

22. A method of treating myofascial pain comprising administering a therapeutically effective amount of the composition of claim 1 to a patient in need thereof to thereby treat said myofascial pain.

* * * * *